United States Patent [19]

Erhardt

[11] 4,182,859
[45] Jan. 8, 1980

[54] PROCESS FOR THE PREPARATION OF 2′-DEOXYRIBOFURANOSYL NUCLEOSIDES

[75] Inventor: Siegfried Erhardt, Esslingen-Zel, Fed. Rep. of Germany

[73] Assignee: Robugen GmbH Pharmaceutische Fabrik, Esslingen-Zel, Fed. Rep. of Germany

[21] Appl. No.: 904,570

[22] Filed: May 10, 1978

[30] Foreign Application Priority Data

May 12, 1977 [DE] Fed. Rep. of Germany ....... 2721466

[51] Int. Cl.² ............................................. C07H 17/00
[52] U.S. Cl. ....................................... 536/23; 424/180
[58] Field of Search ............................... 536/23, 24

[56] References Cited

U.S. PATENT DOCUMENTS

| 3,352,849 | 11/1967 | Shen et al. | 536/23 |
| 3,354,160 | 11/1967 | Duschinsky | 536/23 |
| 3,531,464 | 9/1970 | Ryan et al. | 536/23 |
| 3,708,469 | 1/1973 | Vorbrüggen et al. | 536/23 |
| 3,748,320 | 7/1973 | Vorbrüggen et al. | 536/23 |
| 3,817,980 | 6/1974 | Vorbrüggen et al. | 536/23 |
| 4,082,911 | 4/1978 | Vorbrüggen | 536/23 |

OTHER PUBLICATIONS

Kulikowski, T. and Shugar, D., J. Med. Chem., 1974, vol. 17, 269–273.

Primary Examiner—Johnnie R. Brown
Assistant Examiner—Blondel Hazel
Attorney, Agent, or Firm—Birch, Stewart, Kolasch and Birch

[57] ABSTRACT

2′-Deoxyribofuranosyl nucleosides having the formula:

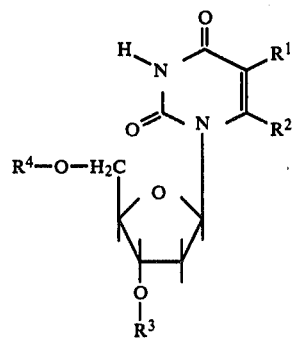

, wherein $R^1$ is a hydrogen atom, a straight-chain or branched alkyl group of 1–6 carbon atoms, a phenyl or benzyl group, a methoxy group, a halogen atom, a nitro group, a nitrile group or an amino group which can be mono- or disubstituted by alkyl of 1–6 carbon atoms, or in which the nitrogen atom thereof is part of a 5- or 6-membered ring, or a perfluoroalkyl group of 1–6 carbon atoms; $R^2$ is a hydrogen atom or a halogen atom; and $R^3$ and $R^4$ are benzoyl, tolyl, p-chlorobenzoyl or p-nitrobenzoyl, which comprises reacting a 1-halogen derivative of a blocked 2-deoxy-D-ribose with a silylated pyrimidine derivative in an alkyl nitrile solvent in the presence of a mercury (II) salt at a temperature of about −10° to about 40° C. The biologically active β-anomers can be separated from the resulting reaction mixture readily and in high yield. The disclosed process is particularly suitable as a means for producing the known antiviral compound β-5-ethyl-2′-deoxyuridine.

13 Claims, No Drawings

PROCESS FOR THE PREPARATION OF 2'-DEOXYRIBOFURANOSYL NUCLEOSIDES

The invention relates to a process for the preparation of 2'-deoxyribofuranosyl nucleoside derivatives having the formula:

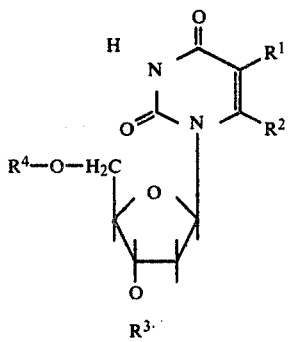

wherein:

$R^1$ represents a hydrogen atom, or a straight-chain or branched alkyl group of 1–6 carbon atoms, preferably the ethyl group; a phenyl or benzyl group; a methoxy group; a halogen atom (particularly fluorine or chlorine); a nitro group; a nitrile group or an amino group which can optionally be mono- or disubstituted by alkyl residues of 1–6 carbon atoms, or in which the nitrogen atom thereof can be part of a 5- or 6-membered ring, preferably the piperidine or morpholine ring; or a perfluoroalkyl group of 1–6 carbon atoms, especially a $CF_3$-group;

$R^2$ is a hydrogen atom or a halogen atom, especially a fluorine or chlorine atom; and $R^3$ and $R^4$ represent a benzoyl, tolyl, p-chlorobenzoyl, or p-nitrobenzoyl group.

Several processes have been known for the preparation of pyrimidine nucleosides; see, for example, T. Kulikowski and D. Shugar, *J. Med. Chem.*, 1974, vol. 17, pp. 269–273; and East German Pat. No. 98,930. During the production of 2'-deoxyribofuranoxyl nucleosides, two stereoisomeric compounds are obtained in all cases, namely the α- and β-anomers. These two stereoisomers can be separated only under great difficulties. Since only the β-anomer is pharmacologically active, the essential aspect of all processes for the preparation of deoxyribofuranosyl nucleosides is the obtaining and separating of the β-anomer. This can be accomplished in the conventional procedures only by very expensive fractional crystallization processes and/or chromatographic separation methods. In the aforementioned process by T. Kulikowski and D. Shugar, a silylated pyrimidine is reacted with 1-halogen sugars or 2-deoxy-D-ribose in acetonitrile in the presence of mercury(II) bromide. However, this process yields a poor α:β ratio (maximally α:β=5:2), and the total yield is merely 42% of theory. Only the α-anomer can be obtained in the pure form by recrystallization. The important β-anomer is separated by means of chromatographic methods. Finally, attention is invited to the process described in DOS [German Unexamined Laid-Open Application] No. 1,919,307 operating with Friedel-Crafts catalysts, wherein difficulties are encountered in working up the reaction mixture inasmuch as emulsions or colloids are produced.

As is known, nucleosides are compounds which occur naturally in the body and are made up of either a purine or pyrimidine base and a sugar. In case of the 2'-deoxyribofuranosyl nucleosides, deoxyribose yields the sugar moiety. By phosphorylation, the nucleotides are obtained from the nucleosides; the nucleotides, in turn, are the monomeric building blocks of nucleic acid.

It has been found that nucleosides can find use in medicine (W. H. Prusoff and D. C. Ward, Nucleoside Analogs with Antiviral Activity, *Biochem. Pharmac.* 25, 1233 [1976]). Exemplary thereof are 5-ethyl-2'-deoxyuridine (K. K. Gauri, G. Malorny, and W. Schiff, *Chemotherapy*, 14, 129 [1969]) and 5-iodo-2'-deoxyuridine (H. E. Kaufman, E. L. Martola, and C. Dohlman, *Arch. Ophthalmol.*, 68, 235 [1962]), both of which have antiviral activity.

As noted above, practically only the β-anomers of this class of compounds possess an interesting biological effectiveness.

Therefore, the present invention relates to providing a process for the preparation of 2'-deoxyribofuranosyl nucleosides which makes it possible to separate the biologically active β-anomer in a high yield and in an economical and technically simple procedure.

This objective is attained by means of the process of the present invention, which comprises reacting the 1-halogen derivative, preferably the 1-chlorine derivative, of a blocked 2-deoxy-D-ribose of Formula II:

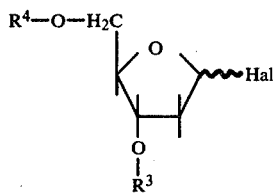

wherein $R^3$ and $R^4$ have the above-indicated meanings, with a silylated pyrimidine derivative of Formula III:

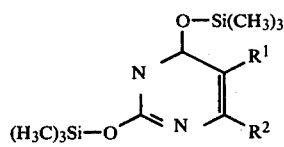

wherein $R^1$ and $R^2$ have the above-indicated meanings, in an alkyl nitrile of Formula IV:

$$R^5—C\equiv N \qquad (IV)$$

wherein $R^5$ represents a straight-chain or branched alkyl group of 1–4 carbon atoms, in the presence of mercury(II) salts at a temperature of from about −10° to +40° C.; and removing the thus-precipitated β-anomer from the reaction mixture, preferably by filtration.

The reaction is preferably conducted at a temperature of between about 0° C. and room temperature (about 25° C.).

The production of the 1-halogen derivative of a blocked 2'-deoxy-D-ribose has been described, for example, in *Chem. Ber.*, 93, 2777 (1960).

The silylated pyrimidine derivatives of Formula III are obtainable, for example, by reacting the corresponding uracil derivative with a typical silylating agent, such as hexamethyldisilazane or trimethylchlorosilane, or a mixture of these two reagents; see, for example, E. Wittenburg, *Chem. Ber.*, 99, 2380 (1966).

Preferred nitrile solvents are the alkyl nitriles such as acetonitrile, propionitrile, and butyronitrile. The most preferred nitrile solvent is acetonitrile.

The bromide, chloride, or acetate is the preferred mercury (II) salt; the most preferred mercury(II) salt is mercury(II) bromide.

In the above-described reaction, the desired β-anomer is surprisingly precipitated as the only insoluble component in practically pure form when the reaction mixture is allowed to stand at a temperature of between about −3° and 20° C., whereas the α-anomer remains dissolved and precipitates (after separation of the β-anomer) only when the reaction mixture is allowed to stand for a rather long time in a refrigerator. The thus-obtained product can be isolated in a practically pure state by simple vacuum filtering; residues of the reaction solution can be eliminated by washing with a small amount of acetonitrile or another solvent. Surprisingly, the thus-obtained product is practically free from mercury impurities, which represents a further essential advantage over the prior art processes.

Advantageously, 1–10 liters of nitrile solvent, preferably 2–3 liters of nitrile solvent, are utilized during the reaction per mole of compound of Formula II.

A catalytic amount of the mercury(II) salt is employed in the reaction. However, advantageously, the molar ratio of the compound of Formula II to the mercury catalyst is generally about 10:1, preferably 5:1.

Although the β-anomer prepared according to the process of this invention is isolated in practically pure form, it is possible, for safety's sake, in order to remove any possibly present mercury traces, to extract a solution of the product obtained according to the invention in a chlorinated hydrocarbon, preferably dichloroethane or chloroform, with a 10% aqueous KI solution, and then to conduct a subsequent washing step with water. After evaporating the solvent under vacuum, the desired compound remains as the residue.

The blocking groups are removed in a conventional fashion, for example, by treatment with sodium methylate in methanol; see, for example, the above-mentioned work by T. Kulikowski and D. Shugar.

The process of this invention is suitable, in particular, for producing the conventional antivirally active compound β-5-ethyl-2'-deoxyuridine.

The following examples are given merely as illustrative of the present invention and are not to be considered as limiting.

EXAMPLE 1

1-[2'-Deoxy-3',5'-di-O-(p-chlorobenzoyl)-β-D-ribofuranosyl]-5-ethyluracil

A 1-liter round flask is charged with 500 ml. of acetonitrile (dehydrated), and 62.6 g. (0.220 mole) of 2,4-bis-O-trimethylsilyloxy-5-ethylpyrimidine is added thereto. To the colorless, clear solution is added 86 g. (0.200 mole) of 3,5-di-O-(p-chlorobenzoyl)-2-deoxy-D-ribofuranosyl chloride. The white suspension is combined under agitation with 14.4 g. (0.04 mole) of mercury(II) bromide. The reaction mixture is clarified within 1–2 minutes and now exhibits a slightly yellow color. Under the exclusion of moisture, the mixture is further agitated at room temperature. After about 10 minutes, a white substance begins to precipitate. After 1 hour, the batch, already containing a large amount of precipitated substance, is placed in a refrigerator overnight. Then, the reaction mixture is vacuum-filtered and the residue of the filtration is washed with a small amount of acetonitrile. The residue is dissolved in approximately 500 ml. of warm chlorinated hydrocarbon, preferably dichloroethane or chloroform. After the solution has cooled, it is extracted with 1. 300 ml. of 10% aqueous KI solution and
2. 100 ml. of water.

The solvent is evaporated under vacuum from the organic phase, thus obtaining a white residue having a melting point of 196°–197° C.

From comparative investigations with the use of thin-layer chromatography, it can be seen that the β-anomer is thus obtained, as also demonstrated by the melting point.

Yield: 65.3 g. (61.3% of theory).

If the filtrate is returned into the refrigerator, 28.9 g. of a compound having a slightly yellow color and a melting point of 186°–187° C. is obtained by working the mixture up as described above. An investigation shows that the β-anomer is the product of this case.

Yield: 28.9 g (27.1%)

The total yield is accordingly 94.2 g. (88.3%).

EXAMPLE 2

1-[2'-Deoxy-3',5'-di-O-(p-tolyl)-β-D-ribofuranosyl]-5-ethyluracil 3.41 g. (12.00 millimoles) of the bis-silyl compound of 5-ethyluracil is dissolved in 80 ml. of acetonitrile (dehydrated), and then 3.9 g. (10 millimoles) of 3,5-di-O-(p-tolyl)-2-deoxy-D-ribofuranosyl chloride is added thereto. Under agitation, 1.75 g. (4.86 millimoles) of HgBr$_2$ is thereafter introduced into the reaction mixture. The latter is stirred at room temperature for one day and the thus-precipitated compound is removed by vacuum-filtration.

The product is worked up as disclosed in Example 1, thus obtaining 2.9 g. (59.2% of theory) of β-anomer with the melting point of 198°–199° C. From the mother liquor, another 1.7 g. (34.7%) of α-anomer, melting point 162°–163° C., is additionally obtained.

The total yield is, therefore, 4.6 g. (93.8%).

EXAMPLE 3

1-[2'-Deoxy-3',5'-di-O-(p-chlorobenzoyl)-β-D-ribofuranosyl]-5-butyluracil 3.44 g. (11 millimoles) of the bis-silyl compound of 5-butyluracil is dissolved in 50 ml. of acetonitrile (dehydrated), and then 4.3 g. (10 millimoles) of 3,5-di-O-(p-chlorobenzoyl)-2-deoxy-D-ribofuranosyl chloride is added thereto. Under agitation, 1.4 g. (4 millimoles) of HgBr$_2$ is then added to the reaction mixture. The latter is stored in a refrigerator for 2 days; after vacuum-filtering and working up as described in Example 1, 3.1 g. (55.3% of theory) of β-anomer is obtained, melting point 166°–168° C.

By recrystallization from ethanol, the melting point is raised to 172°–173° C.

EXAMPLE 4

N-[2',-Deoxy-3',5'-di-O-(p-chlorobenzoyl)-β-D-ribofuranosyl]-5-ethyl-6-chlorouracil 3.5 g. (11 millimoles) of the bis-silyl compound of 5-ethyl-6-chlorouracil is dissolved in 50 ml. of acetonitrile (dehydrated), and then 4.3 g. (10 millimoles) of 3,5-di-O-(p-chlorobenzoyl)-2-deoxy-D-ribofuranosyl chloride is added thereto. Under agitation, 1.4 g. (4 millimoles) of HgBr₂ is then introduced.

After 23 hours of agitation at room temperature, the mixture is vacuum-filtered and worked up as described in Example 1.

The thus-obtained product is 1.1 g. (19.7%) of a brown, crystalline compound (pure as determined by thin-layer chromatography).

After purification, 0.8 g. (14.3%) of a white compound is obtained having a melting point of 161°–162° C.

In a manner analogous to that shown in the above Examples, the process of this invention is particularly suitable for the preparation of the following compounds:

(1) 1-[2'-deoxy-3',5'-di-O-(p-chlorobenzoyl)-β-D-ribofuranosyl]-5-ethyl-6-fluorouracil (2) 1-[2'-deoxy-3',5'-di-O-(p-tolyl)-β-D-ribofuranosyl]-5-methyl-6-fluorouracil (3) 1-[2'-deoxy-3',5'-di-O-(p-tolyl)-β-D-ribofuranosyl]-5-nitrouracil (4) 1-[2'-deoxy-3',5'-di-O-(p-chlorobenzoyl)-β-D-ribofuranosyl]-5-methoxymethyluracil (5) 1-[2'-deoxy-3',5'-di-O-(p-chlorobenzoyl)-β-D-ribofuranosyl]-5-dimethylaminouracil (6) 1-[2'-deoxy-3',5'-di-O-(p-chlorobenzoyl)-β-D-ribofuranosyl]-5-morpholinouracil (7) 1-[2'-deoxy-3',5'-di-O-(p-chlorobenzoyl)-β-D-ribofuranosyl]-5-mercaptomethyluracil (8) 1-[2'-deoxy-3',5'-di-O-(p-chlorobenzoyl)-β-D-ribofuranosyl]-5-cyclohexyluracil (9) 1-[2'-deoxy-3',5'-di-O-(p-chlorobenzoyl)-β-D-ribofuranosyl]-5-trifluoroethyluracil.

The invention being thus described, it will be obvious that the same may be varied in many ways. Such variations are not to be regarded as a departure from the spirit and scope of the invention, and all such modifications are intended to be included within the scope of the following claims.

What is claimed is:

1. A process for the preparation of substantially pure β-anomers of 2'-deoxyribofuranosyl nucleosides of the formula:

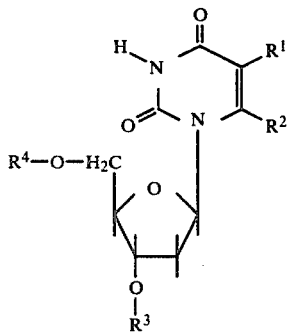

wherein
R¹ represents a hydrogen atom, a straight-chain or branched alkyl group of 1 to 6 carbon atoms, a phenyl or benzyl group, a methoxy group, a halogen atom, a nitro group, a nitrile group, or an amino group which is unsubstituted or mono- or disubstituted by alkyl residues of 1 to 6 carbon atoms, or in which the nitrogen atom thereof can be part of a 5- or 6-membered ring, or a perfluoroalkyl group of 1 to 6 carbon atoms;
R² is a hydrogen atom or a halogen atom; and
R³ and R⁴ represents a benzoyl, tolyl, p-chlorobenzoyl, or p-nitrobenzoyl group, which comprises reacting a 1-halogen derivative of a blocked 2-deoxy-D-ribose having the formula:

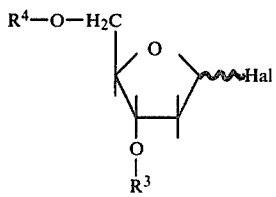

wherein Hal represents a halogen atom, with a silylated pyrimidine derivative having the formula:

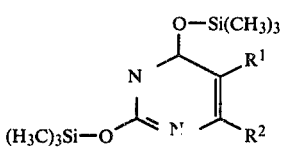

wherein R¹, R², R³ and R⁴ have the above-indicated meanings, in an alkyl nitrile solvent having the formula:

          IV wherein R⁵ represents a straight-chain or branched alkyl group of 1 to 4 carbon atoms, and in the presence of a mercury(II) salt at a temperature of about −10° to about +40° C.; precipitating the desired β-anomer as the only insoluble component by allowing the reaction mixture to stand at a temperature of between about −3° C. to 20° C.; and separating the thus-precipitated β-anomer from the reaction mixture.

2. The process of claim 1, wherein the mercury(II) salt employed is HgBr₂, and the nitrile solvent employed is acetonitrile.

3. The process of claim 1, wherein R¹ is an ethyl group.

4. The process of claim 1, wherein R¹ is a piperidine ring.

5. The process of claim 1, wherein R¹ is a morpholine ring.

6. The process of claim 1, wherein R¹ is a CF₃ group.

7. The process of claim 1, wherein R² is a fluorine or chlorine atom.

8. The process of claim 1, wherein the Hal in said blocked 2-deoxy-D-ribose derivative is a chlorine atom.

9. The process of claim 1, wherein said nitrile solvent is selected from the group consisting of acetonitrile, propionitrile and butyronitrile.

10. The process of claim 1, wherein said mercury(II) salt is selected from the group consisting of HgBr₂, HgCl₂ and Hg(CH₃COOO)₂.

11. The process of claim 1, wherein the β-anomer is separated from the reaction mixture by filtration.

12. The process of claim 1, wherein the recovered β-anomer is extracted and washed in order to remove any traces of mercury.

13. The process of claim 1, wherein the β-anomer is 1-[2'-deoxy-3',5'di-O-(p-chlorobenzoyl)-β-D-ribofuranosyl]-5-ethyluracil.

* * * * *